(12) United States Patent
Gartner et al.

(10) Patent No.: US 6,835,783 B1
(45) Date of Patent: Dec. 28, 2004

(54) MANUFACTURE OF SUPERABSORBENTS IN HIGH INTERNAL PHASE EMULSIONS

(75) Inventors: Herbert A. Gartner, Baden-Baden (DE); Steven W. Mork, Midland, MI (US); Heike Herr, Achern (DE); Reed A. Shick, Midland, MI (US); John Klier, Midland, MI (US); Christopher J. Tucker, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 09/913,621

(22) PCT Filed: Feb. 23, 2000

(86) PCT No.: PCT/US00/04573

§ 371 (c)(1),
(2), (4) Date: Aug. 15, 2001

(87) PCT Pub. No.: WO00/50096

PCT Pub. Date: Aug. 31, 2000

Related U.S. Application Data

(60) Provisional application No. 60/121,329, filed on Feb. 24, 1999.

(51) Int. Cl.[7] .......................... A61L 15/24; A61L 15/60; C08F 2/32
(52) U.S. Cl. .................... 525/329.7; 523/337; 524/801; 427/133; 427/372.2; 427/375; 427/385.8; 427/393.5; 427/445
(58) Field of Search ................. 525/329.7; 523/337; 524/801, 458; 427/133, 372.2, 375, 385.5, 393.5, 445

(56) References Cited

U.S. PATENT DOCUMENTS

| | | | |
|---|---|---|---|
| 3,624,019 A | 11/1971 | Anderson et al. | |
| 3,926,891 A | 12/1975 | Gross et al. | |
| 4,071,650 A | 1/1978 | Gross | |
| 4,076,928 A | 2/1978 | Gross | |
| 4,117,184 A | 9/1978 | Erickson et al. | |
| 4,339,371 A | * 7/1982 | Robinson et al. | ........... 524/310 |
| 4,973,632 A | * 11/1990 | Nagasuna et al. | .......... 526/200 |
| 5,387,207 A | 2/1995 | Dyer et al. | |
| 5,994,419 A | * 11/1999 | Collette et al. | ............... 521/64 |
| 6,048,908 A | * 4/2000 | Kitagawa | ..................... 521/56 |

FOREIGN PATENT DOCUMENTS

| | | |
|---|---|---|
| AU | 10105/88 | 4/1988 |
| EP | 0349240 | 4/1997 |
| KR | 915506 | 7/1991 |
| WO | 93/18223 | 9/1993 |
| WO | 95/01146 | 1/1995 |
| WO | 95/26209 | 10/1995 |

* cited by examiner

*Primary Examiner*—Kelechi C. Egwim

(57) ABSTRACT

The present invention refers to a high internal phase polyelectrolyte emulsions which are useful for the manufacture of superabsorbent polymers having two phases: i) a continuous oil phase and the ii) a dispersed aqueous phase containing the aqueous monomer solution prior to polymerization and the polyelectrolyte in water-soluble, or water-swellable or very slightly crosslinked form after polymerization, wherein the polymerization occurs in the dispersed aqueous phase and wherein the dispersed aqueous phase contains a high concentration of polyelectrolyte. The present invention also refers to a process for preparing such emulsions and for inverting these emulsions so as to form films or other patterns of the superabsorbent polymer. Absorbent structures containing SAP films or other patterns prepared by the present invention are also contemplated.

10 Claims, No Drawings

MANUFACTURE OF SUPERABSORBENTS IN HIGH INTERNAL PHASE EMULSIONS

This application claims the benefit of provisional application Ser. No. 60/121,329 filed Feb. 24, 1999.

The present invention refers to superabsorbent polymers made from water-in-oil emulsions as well as to a process for preparing such superabsorbent polymers.

Typically, superabsorbent polymers (SAP's) have been prepared by gel polymerization of water-soluble monomers in aqueous solution. Certain additives, such as cross linking agents, may be incorporated into the monomer mixture. The product of the polymerization process is then typically dried and subjected to mechanical means of particle size reduction and classification including chopping, grinding, and sieving. Optionally, the product may be subjected to a post-treatment to improve its quality and performance, especially its ability to absorb aqueous fluids. Such post-treatments include surface post-crosslinking, heat treatment and heat treatment in the presence of an oxidizing agent, such a sodium or potassium chlorate.

Superabsorbent polymers are primarily used in personal care products which absorb body fluids, for example, baby diapers, adult incontinence products and feminine hygiene products. In these applications, SAP particles are incorporated into absorbent structures which contain, for example, synthetic and natural fibers which may or may not be in the form of paper based woven and non-woven structures, and toughened masses of fibers, such as fluff pads. The materials used in such structures can rapidly acquire aqueous fluids, distribute the fluids over the whole absorbent structure and absorb and retain them. The absorbent structures, in the absence of SAP particles, have limited absorption capacity, are bulky due to the large amount of material needed to provide acceptable absorption capacity, and inadequately retain fluid under pressure.

However, there is a trend to design absorbent structures having various SAP concentrations distributed in the absorbent structure in order to achieve a desired absorbency profile of the absorbent device. See, for example, WO 95/26209. It is also a trend to apply two or more SAP's which differ in their absorption characteristics and to distribute them in specific patterns within the structure. See, for example, WO 95/01146. In such structures, it is essential that the SAP(s), distributed in such complicated patterns, stays in the desired region, especially under use conditions. Furthermore, it would be desired to prepare superabsorbent polymers which could be easily shaped into various different forms and fixed onto the relevant structure in any desired concentration. With the prior art granular SAP's, as described above, such goals would only be achievable through burdensome handling and fixing of the ground SAP particles and economically unfeasible manufacturing processes for the fixing application of the SAP particles to the absorbent structures.

Thus, alternative manufacturing processes for superabsorbent polymers and even new superabsorbent polymers which could be employed in absorbent structures having a specific absorbency profile are sought.

U.S. Pat. No. 3,926,891 refers to water-swellable polyacrylate articles made from a solution of the polyacrylate having an effective amount of a soluble crosslinking agent therein by heating and/or drying the solution. The polyacrylate solution is made from a polyacrylate by saponification and the crosslinking agent is then added.

U.S. Pat. No. 4,071,650 and U.S. Pat. No. 4,076,928 refer to water-swellable articles made from copolymers having a copolymerized crosslinker, methods for preparing such articles, as well as to compositions containing a copolymerized crosslinker useful to make said articles. The articles are crosslinked by heating and/or removing substantially all of the water from the precursor composition.

U.S. Pat. No. 4,117,184 is directed to water-swellable aerated films and laminates made from solutions of carboxylic polyelectrolytes and methods for preparing same. The films and laminates are cured and/or crosslinked with a polyfunctional or difunctional crosslinking agent that is reactive with carboxylate groups by heating and/or removing substantially all of the water and/or alcohol from the precursor composition. The solutions are mechanically aerated prior to the curing step.

U.S. Pat. No. 4,339,371 refers to water-in-oil emulsions containing high concentrations of water-soluble polymers which are prepared by incorporating therein an oil-soluble, water-insoluble polymeric surfactant prepared from maleic anhydride and a comonomer.

AU-A-10105/88 describes the manufacture of non-crosslinked poly(acrylic acid) and its salts using an inverse water-in-oil emulsion polymerization process that requires a co-water-in-oil emulsifier which is a $C_{12}$–$C_{22}$ fatty acid, and preferably is oleic acid.

WO 93/18223 teaches a process for treating a substrate with a superabsorbent material in which process a layer of a water-in-oil SAP-containing emulsion, containing the superabsorbent material in its aqueous phase, is applied to the substrate in such a manner that 0.3 to 40 weight percent, calculated on its dry weight, of the superabsorbent material is applied to the substrate. After this step, the liquid constituents of the emulsion are wholly or partially removed from the substrate. Only crosslinked materials are employed in this patent application. Disclosed examples of superabsorbent materials include crosslinked polyacrylic acid partially neutralized into the sodium salt. The teachings of this reference do not cover any film formation, homogenization of the spread to form a homogeneous gel matrix, or post-crosslinking. Furthermore, the articles made in accordance with the teachings of this reference provide a high gel blocking behavior.

Korean Patent 915 506 describes the preparation of a water absorbable resin in the form of flakes from a crosslinked, partly neutralized polyacrylic acid which is provided in the form of a water-in-oil emulsion. After partly drying and shaping (flattening) of the polymer emulsion with the aid of a drum dryer, the surface of the flakes obtained is post-crosslinked with diglycidyl ethers.

None of these patents or patent applications, however, describe a process for preparing a SAP of desired properties from highly concentrated precursor polymers which have a high enough molecular weight and which are easily applicable to absorbent structures whereby the concentration, pattern and form of the SAP distribution can be easily designed. Therefore, there still remains the need for such a process and the SAP's resulting therefrom.

Those needs are met by the present invention, which provides high internal phase polyelectrolyte emulsions which are useful for the manufacture of superabsorbent polymers. The present invention also provides superabsorbent polymers made from such high internal phase polyelectrolyte emulsions. More specifically, the present invention provides processes for the preparation of high internal phase linear or very slightly crosslinked polyelectrolyte water-in-oil emulsions and processes for inverting such water-in-oil emulsions, followed by polymer crosslinking, so as to obtain highly concentrated superabsorbent polymers.

Accordingly, the present invention provides SAP's in the conventional powder form, but preferably, the present invention can be employed to prepare alternative forms, such as films or various patterns; or the SAP's can be produced as combinations of these forms with any possible support material.

Surprisingly, it has been found that one of the key advantages of the present invention is that the water-in-oil emulsions can be produced and applied in a highly concentrated but still liquid or easily spreadable form. They can easily be applied in any desired shape onto any desired support material and are efficiently transformed into SAP's. Advantageously, the application of the polyelectrolyte water-in-oil emulsion allows for the use of very high molecular weight polymers in high concentration. Furthermore, another advantage of the present invention is that the high viscosity, which aqueous solutions of those polymers typically possess and which would make spreading and shaping of concentrated solutions extremely hard, if not impossible, only develops with the present invention during inversion, that is, after shaping has been completed.

In one aspect, the invention is a high internal phase polyelectrolyte emulsion which is useful for the manufacture of a superabsorbent polymer, the emulsion having two phases: i) a continuous oil phase and ii) a dispersed aqueous phase containing polyelectrolyte, wherein the dispersed aqueous phase contains a concentration of polyelectrolyte which is from 10 to 50 percent, based on the total aqueous phase.

In another aspect, the invention is a process for preparing superabsorbent structures comprising:

(a) preparing a high internal phase water-in oil emulsion comprising, in its aqueous dispersed phase, at least one hydrophilic monomer in aqueous solution and an initiator, (b) polymerizing the monomer in the aqueous dispersed phase to form a precursor polymer, (c) mixing the water-in-oil emulsion containing the precursor polymer with a post crosslinker and, optionally a plasticizing agent, (d) spreading, patterning or casting the emulsion resulting from step (c) onto a support material, (e) allowing or inducing coalescence of the aqueous phase under conditions sufficient to allow the emulsion to form a homogeneous polymer gel structure, and (f) drying and post crosslinking the formed gel material at a temperature sufficient to dry and cure the material, and (g) optionally, post-treating the material obtained in step (f) by post-heat treating the material, by surface modifying the material, by surface post-crosslinking the material, or by any combination of these post-treatments.

The SAP's according to the present invention are made from a water-in-oil emulsion containing a high molecular weight, optionally very slightly crosslinked polyelectrolyte (superabsorbent precursor polymer). It is desirable that the water-in-oil emulsions of the present invention contain a high ratio of water phase to oil phase in order provide high polymer concentration and low amounts of oil. The high internal phase emulsion is made as a water-in-oil emulsion containing a water-soluble or very slightly crosslinked polyelectrolyte in its aqueous or dispersed phase to a degree that it can, after polymerization, form a substantially homogenous gel matrix which can be easily crosslinked with a suitable post-crosslinker capable of reacting with functional groups of the polymer.

The water-in-oil emulsion of the present invention consists of two phases: i) a continuous oil phase and the ii) a dispersed aqueous phase containing the aqueous monomer solution prior to polymerization and the polyelectrolyte in water-soluble, or water-swellable or very slightly crosslinked form after polymerization. The dispersed phase is the phase where the polymerization occurs and contains a high concentration of polyelectrolyte. For economical reasons, the monomer concentration in the precursor polyelectrolyte in the aqueous or dispersed is preferably as high as possible. Suitable concentrations are in the range of 20 to 45 percent of polyelectrolyte based on the total aqueous phase. Furthermore, after polymerization, the dispersed phase consists of small, rubber-like gel particles, in view of the high molecular weight of polyelectrolyte.

Thus, in a preferred embodiment, the present invention refers to a high internal phase polyelectrolyte emulsions, which are useful for the manufacture of superabsorbent polymers, having two phases: i) a continuous oil phase and the ii) a dispersed aqueous phase containing the aqueous monomer solution prior to polymerization and the polyelectrolyte in water-soluble, or water-swellable or very slightly crosslinked form after polymerization, wherein the polymerization occurs in the dispersed aqueous phase and wherein the dispersed aqueous phase contains a high concentration of polyelectrolyte.

The continuous oil phase comprises a hydrophobic organic solvent having a boiling point in the range of 60° C. to 250° C. and typically also contains an emulsion-stabilizing amount of an emulsion surfactant, a suitable dispersing agent, or a combination thereof. The emulsion has an oil phase of not more than 30 percent by weight. The ratio of the dispersed aqueous phase to the continuous oil phase is preferably as high as possible. Ratios in the range from 70:30 to 99:1, preferably from 73:27 to 98:2, more preferably from 75:25 to 95:5, most preferably 75:25 to 90:10, have successfully been applied.

"Roll goods", as used herein, means a combination of a support material as used or as being usable in absorbent structures or devices for fluid management and SAP's according to the present invention. The SAP(s) is(are) fixed onto the support material in the desired form, concentration and distribution, and the final material may be supplied in a rolled-up form from which it can be directly dispensed to make articles, such as, for example, diapers.

"Water-soluble", as used herein to describe a polymer, means a substance that is substantially soluble in water, that is, it turns from aqueous gel, as represented by the dispersed, polymerized phase of the emulsions of the present invention, to a solution upon contact with sufficient water or aqueous solution. Specifically, the process of the present invention allows the manufacture of SAP films, laminates or absorbent structures in the form of "roll goods".

"Water-swellable", as used herein, means the SAP powder or SAP gel particles, as present in the water-in-oil emulsions of the present invention, which are capable of absorbing water or aqueous fluids and thereby increasing their original volume many times, such as at least 10 times, more preferably at least 20 times.

"Very slightly crosslinked" as used herein, means that the polymer possesses sufficient non-crosslinked (not fixed to network) polymer molecules or sufficient high molecular weight chain ends which will, after emulsion inversion, provide sufficient bridging between the polymer particles by molecular diffusion so that at least agglomerates of strength suitable for the intended end use application of the polymer can be formed. A very slightly crosslinked polymer can be formed when no polymerization crosslinker is employed. For example, the polymerization product may contain a fraction of gel or microgels that may have formed during polymerization due to chain transfer to polymer grafting in the absence of added crosslinker.

The term "homogeneous polymer gel structure" as used herein refers to the microstructure of the polymer gel. Gel, or polymer, particles are formed in the polymerization step of the invention. While it is possible to recover the particles as such, it is preferred to allow the particles to stand, for example in the presence of added water, under conditions sufficient to allow the particles to diffuse into each other, thus forming a homogeneous polymer gel structure.

"High molecular weight" as used herein, means a weight average molecular weight (Mw) of at least 1,500,000. The method employed to measure the molecular weight of the polymers prepared according to the present invention is described below.

"Dispersity (D)", as used herein, shall mean the ratio of weight average molecular weight (Mw) to number molecular average weight (Mn), (Mw/Mn). Preferred dispersity values are of no more than 6, more preferably 4 or less. Dispersity is also referred to as molecular weight distribution.

The terms "inverting" and "inversion" as used herein in connection with emulsions also means coalescing or coalescence.

The present invention further provides a process comprising:

(a) preparing a high internal phase water-in oil emulsion containing, in its aqueous or dispersed phase, at least one hydrophilic monomer in aqueous solution and a suitable initiator, (b) polymerizing the aqueous or dispersed phase, (c) mixing the polymerized water-in-oil emulsion containing the superabsorbent precursor polymer with suitable post-crosslinkers, inversion agents, and, optionally a plasticizing agent, (d) spreading or casting said emulsion on a desired support material into the desired shape, (e) allowing the cast emulsion to invert from a water-in-oil emulsion into an oil-in-water emulsion for a time sufficient to allow the emulsion to invert and for the polymer material to homogenize, in order to provide a homogeneous polymer gel structure, and (f) drying and curing (crosslinking) the formed gel material at a temperature sufficient to dry and cure the material, and (g) optionally, post-treating the material obtained in step (f) either by post-heat treating such material, surface modifying the material or by surface post-crosslinking of such material.

The present invention further provides various techniques, but is not limited to these techniques, to invert the high internal phase emulsions of the present invention. The inversion of the emulsions of the present invention may be accomplished using, for example, the following techniques: 1) solvent extraction, 2) evaporation of the organic phase, 3) application of surfactant(s) having a high hydrophilic lipophilic balance (HLB), 4) application of low critical solution temperature (LCST) solvents, or 5) application of metal oxide powders.

As mentioned above, the aqueous or dispersed phase is made of suitable water-soluble radically polymerizable monomers and other components which constitute the polyelectrolyte. Suitable polyelectrolytes include, but are not limited to hydrophilic polymers which, in crosslinked form, are capable of absorbing large quantifies of fluids. In particular, hydrophilic polymers useful in this invention are those typically employed to make SAP's, such as water-absorbent polymers which contain carboxyl moieties. Preferably, at least about 0.01 equivalent of carboxyl groups are present per 100 grams of the water-absorbent resin.

Among preferred carboxyl containing water-absorbent polymers are those derived from one or more ethylenically unsaturated carboxylic acids, ethylenically unsaturated carboxylic acid anhydrides or salts thereof. Additionally, the polymers may include comonomers known in the art for use in water-absorbent resin particles or for grafting onto the water-absorbent resins, including comonomers such as acrylamide, a vinyl pyrrolidone, a vinyl sulphonic acid or a salt thereof, acrylamidopropane sulfonic acid (AMPS), salts thereof, or phosphonic acid containing monomers, a cellulosic monomer, a modified cellulosic monomer, a polyvinyl alcohol, a starch hydrolyzate, the hydrolyzates of acrylamide copolymers, or crosslinked products of hydrolyzates of acrylamide copolymers.

Preferred ethylenically unsaturated carboxylic acid and carboxylic acid anhydride monomers include, but are not limited to, acrylic acids, such as acrylic acid, methacrylic acid, ethacrylic acid, alpha-chloro acrylic acid, alpha-cyano acrylic acid, beta-methyl acrylic acid (crotonic acid), alpha-phenyl acrylic acid, beta-aryloyloxy propionic acid, sorbic acid, alpha-chlom sorbic acid, angelic acid, cinnamic acid, p-chloro cinnamic acid, beta-styd acrylic acid (1-carboxy-4-phenyl butadiene-1,3), itaconic acid, citraconic acid, mesaconic acid, glutaconic acid, maleic acid, fumaric acid and maleic acid anhydride. More preferably, the carboxyl containing water-absorbent polymers are derived from acrylic acid, methacrylic acid, or a salt thereof, with partially neutralized products of polyacrylic acids and crosslinked products of partially neutralized polyacrylic acids being especially preferred polymers. Mixtures of monomers can be employed.

Especially preferred are alkali metal acrylate-type polymers obtained by copolymerizing 100 parts of an acrylic acid-type monomer composed of 1 to 50 mole percent of acrylic acid and 50 to 99 mole percent of an alkali metal acrylate and 0 to 5 percent by weight of a crosslinkable monomer in aqueous solution in a monomer concentration of at least 20 percent by weight. In another preferred embodiment the alkali metal acrylate-type polymers are obtained by polymerizing acrylic acid and post neutralizing the polymer with an alkali metal base.

There is no limitation to the amount of the carboxyl groups of the water-absorbing resin. Preferably, at least 0.01 equivalent of carboxyl groups are present per 100 grams of the water-absorbent resin. In the case of partially neutralized polyacrylic acid, the proportion of the non-neutralized portion is preferably 1 to 50 mole percent.

Preferably, the polyelectrolyte is partially neutralized polyacrylic add having a degree of neutralization of 60 to 70 percent and a very high molecular weight (Mw), preferably above 1,500,000. The emulsion has a polymer content in the range of 10 to 50, preferably 20 to 40, percent by weight, based on the total aqueous phase. The size of the polymer particles in the emulsion after polymerization is in the range of about 0.1 to 100 microns, more preferably from 1 to 30 microns, depending on the conditions applied for manufacture.

Preferably, the polymer of the invention is not crosslinked until the water-in-oil emulsion is inverted, at which time a post crosslinker is employed. However, a polymerization crosslinker can be optionally employed in the polymerization of the SAP in the water phase. Suitable polymerization crosslinkers are any crosslinkers which are capable of copolymerizing with the monomer(s) to give gel properties suitable for the intended end use application of the polymer. Examples of such polymerization crosslinkers include, but are not limited to, trimethylolpropane triacrylate, ethoxylated trimethylolpropane triacrylate, methylenebisacrylamide, diethyiene glycol diacrylate, ethoxylated diethylene glycol diacrylate, triallylamine, allyl methacrylate, tetraallyoxyethane. Preferred polymerization crosslinkers are trimethylolpropane triacrylate and ethoxylated trimetlylolpropane triacrylate. Mixtures of polymerization crosslinkers can be employed. The preferred amount of polymerization crosslinker is determined by the desired degree of gel modulus. Typically, the polymerization crosslinker is used in amounts ranging from 0.0005 to 5 parts by weight per 100 parts by weight of α, β-ethylenically unsaturated monomer used. More preferably, the amount ranges from 0.1 to 1 part by weight per 100 parts by weight of the α, β-ethylenically unsaturated monomer.

Suitable initiators are any initiators or initiator systems known in the art as useful for the preparation of water-in-oil emulsions or for SAP's, or generally for aqueous solution polymerization. Examples of initiators include, but are not limited to, free-radical initiators, such as oxidation-reduction systems, metal persulfates, peroxides or diazenes. For example, water soluble persulfates such as potassium persulfate, ammonium persulfate, sodium persulfate, and other alkali-metal persulfates, hydrogen peroxide and water soluble azo-compounds such as 2,2'-azobis-(2-amidinopropane) hydrochloride may be used. Some of these initiators, such as hydrogen peroxide, can be combined with reducing substances such as sulfites or amines to form known redox type initiators. Mixtures of initiators can be employed. The initiator is employed in an amount which is sufficient to initiate polymerization and produce a polymer having properties suitable for the intended end use application of the polymer. The total amount of initiators used preferably is from 0.01 to 1.0 weight percent, preferably 0.01 to 0.5 weight percent, based on the total weight of α, β-ethylenically unsaturated monomer reactants.

Suitable as emulsion surfactants are any surfactants which stabilize the emulsion. The emulsion surfactant typically is added to the oil phase, but can be added to the aqueous phase depending on the solubility of the surfactant used. Representatives of such emulsion surfactants include, but are not limited to non-ionic surfactants, sorbitan fatty acid esters such as, for example, sorbitan monooleate and sorbitan monolaurate, glycerol esters such as, for example, glycerol monooleate and glycerol monoricinoleate, phthallc esters, partial fatty acid esters of polyglycerol, the reaction product of oleic acid with isopropanolamide, 12-hydroxystearic acid-polyethylene glycol block copolymers (commercially available as Hypermer B246 and Hypermer B261), fatty acid glycerides, glycerin esters, as well as ethoxylated derivatives thereof; calionic surfactants including, but are not limited to, ammonium salts, such as distearyl dimethyl ammonium chloride and dioleyl dimethyl ammonium dichloride; and anionic surfactants such as bis-tri-decyl sulfosuccinic acid salt; or mixtures thereof. Polymeric surfactants are preferred, with more preferred emulsion surfactants being 12-hydroxystearic acid-polyethylene glycol block copolymers, and commercially available examples of these are Hypermer B246 and B261. The emulsion surfactant can be used alone or in combination. The emulsion surfactant is employed in an amount sufficient to maintain the emulsion during polymerization. Preferably, the emulsion surfactant is employed in an amount not greater than 5 percent by weight of the total emulsion. More preferably, the amount should be less than 2.0 percent by weight of the total emulsion. Advantageously, the process of the invention can be conducted in the substantial absence of a $C_{12}$-$C_{22}$ fatty acid co-water-in-oil emulsifier.

In the present invention, the continuous oil phase can contain, instead of the emulsion surfactant, or in addition to the emulsion surfactant, dispersing agents which are, for example, oil-soluble, surface active polymers or oil-dispersible particulate materials. Representative dispersing agents include, but are not limited to, ethylene-co-maleic anhydride, poly(α-olefin-co-maleic anhydride), ethyl cellulose, poly(lauryl methacrylate-co-acrylic acid), cellulose esters, such as acetates, proplonates and butyrates, and hydrophobic fumed silica or cationic bentonite clays. Mixtures of dispersing agents can be employed. If employed, the dispersing agent is employed in an amount sufficient to maintain the emulsion during polymerization. For example, if the dispersing agent is a cellulose ether, such as ethyl cellulose, methyl cellulose, hydroxyethyl cellulose, hydroxypropyl cellulose, or carboxyethyl cellulose, then it is preferred to employ the dispersing agent in an amount of from 0.1 to 2 percent based on the weight of monomer.

Suitable hydrophobic solvents for the oil phase include any water-insoluble aliphatic or aromatic organic solvent, such as, for example, hydrocarbons having 6 to 20 carbon atoms, kerosene, petrolatums, xylene, toluene, and branched-chain isoparaffins, such as those commercially available from Exxon Chemicals, under the tradename ISOPAR. Preferred organic solvents are heptane, nonane, decane and the isopar-type isoparaffins. A special class of hydrophobic organic solvents which can be employed for the oil phase include those solvents having a boiling point below 100° C. Examples of hydrophobic organic solvents having a boiling point below 100° C. include hexane, cyclohexane and heptane. Mixtures of these solvents can be employed. Typically, the organic solvents are employed in an amount of not more than 30 percent by weight, more preferably less than 20 percent by weight, based on the weight of the total emulsion. Preferably the oil phase is substantially free of vinyl monomers.

The additives useful in the polymerization of the dispersed phase of the emulsions of the present invention include, but are not limited to, chelating agents to chelate metal ions, hydrogen peroxide for bleaching, chlorate compounds as oxidizing agents, and mixtures thereof.

The polymerization step of the process of the invention is conducted under conditions typically employed in the art for the polymerization of oil-in-water emulsions. In a preferred process, the water phase is added to the oil phase. Preferably, the polymerization of the invention is conducted at a temperature of at least 309° C. The post crosslinker preferably is added to the emulsion following polymerization, and the inversion step of the process is then initiated.

Coalescing the internal phase of the invention can be accomplished by any coalescing or inversion techniques know in the art including, for example, adding inversion agents, inducing coalescence by shear forces, and inducing coalescence by acoustical forces.

The inversion agents useful in the present invention will depend on the specific inversion technique chosen to invert the high internal phase emulsions of the present invention. The inversion agent is employed in an amount which is sufficient to invert the emulsion. Mixtures of inversion agents can be employed. Inversion agents useful for inversion technique 1), that is, solvent extraction, include hydrophilic organic solvents, such as alcohol or acetone. Inversion agents useful for inversion technique 2), that is, evaporation of the oil phase, include the hydrophobic organic solvents having a boiling point below 100° C., as defined above. Inversion agents useful for inversion technique 3), that is, application of surfactant(s) having a high hydrophilic lipophilic balance (HLB), include surfactants which are capable of breaking the emulsion and which have a HLB number greater than 10. Representatives of such inversion surfactants include, but are not limited to ethoxylated octyl and nonyl phenols, ethoxylated nonyl phenol formaldehyde resins, polyethylene oxide esters of fatty acids, dioctyl esters of sodium sulfosuccinate, polyethoxylated alcohols and others. Preferred inversion surfactants are polyethoxylated aliphatic secondary alcohol having nine ethylene oxide units and a hydrophobic chain of 12–14 carbon atoms. Preferably, the inversion surfactant is added in an amount of from 0.5 percent by weight to 10 percent by weight, based on the total emulsion. More preferably, from 2 to 5 weight percent of inversion surfactant, and most preferably from 3 to 4 weight percent of inversion surfactant, is employed. In combination with the inversion surfactants, water in a concentration of preferably less than 25 percent by weight, based on the total emulsion, or water-soluble organic solvents or a combination thereof are added to support the inversion.

Inversion agents useful for inversion technique 4), that is, application of low critical solution temperature (LCST) solvents, include dipropylene glycol dimethyl ether, 1,2-hexanediol, ethylene glycol n-butyl ether, propylene glycol propyl ether, as well as other non-ionic polar solvents. Typically, LCST solvents are employed in amounts of from 0.5 weight percent to 10 weight percent, preferably from 0.5 to 5 weight percent and more preferably from 0.5 to 3 weight percent, based on the total emulsion.

inversion agents useful for inversion technique 5), that is, application of metal oxide powders, include titanium dioxide, fumed silica, clays and other particulate oxides. In combination with the metal oxide powders, water in a concentration of preferably less than 25 percent by weight, based on the total emulsion, water-soluble organic solvents or a combination thereof are added to support the inversion.

Suitable post-crosslinkers are any crosslinkers which are capable of reacting with the carboxyl groups of the resulting polymers resulting in crosslinks which give the desired SAP properties. Representatives of such post-crosslinkers include, but are not limited to polyhydroxyl compounds, polyglycidyl ether compounds, polyfunctional aziridine compounds, polyfunctional amine compounds, polyfunctional isocyanite compounds, and alkylene carbonates. Polyfunctional alcohols, di- or polyglycidyl compounds and alkylene carbonates are especially preferred. Mixtures of post-crosslinkers can be employed. The post crosslinker is employed in an amount sufficient to result in a polymer having properties, such as Absorption Under Load and Centrifuge Retention Capacity, which are suitable for the intended end use application of the polymer. Typically, the polymerization crosslinker is used in amounts ranging from 0.0005 to 5 parts by weight per 100 parts by weight of $\alpha$, $\beta$-ethylenically unsaturated monomer used. More preferably, the amount ranges from 0.1 to 1 part by weight per 100 parts by weight of the $\alpha$, $\beta$-ethylenically unsaturated monomer.

Additives which are added after the polymerization but prior to the inversion of the emulsion include plasticizing agents or fillers, such as inert, non-water-soluble organic or inorganic powders. Examples of suitable plasticizing agents include, but are not limited to, glycerin, polyethylene glycol, polypropylene glycol, and ethoxylated and propoxylated agents capable of lowering the glass transition temperature of the SAP significantly. Mixtures of these additives can be employed. For example, mixtures of plasticizing agents can be employed as the plasticizing agent.

The post crosslinker preferably is mixed into the emulsion following polymerization. Preferably, the inversion agent is also added to the emulsion at this time. Following the addition of these materials to the emulsion, the emulsion can be spread into a film or into the desired shape or pattern onto a substrate. Additional water can be added to the emulsion just prior to the spreading step to aid in breaking, or inverting, the emulsion and to aid the formation of a homogeneous polymer gel structure.

The viscosity of the polymer emulsions depends largely on the phase ratio and on the particle size of the dispersed aqueous phase. When determining the viscosity of such emulsions, it is to be kept in mind that the viscosity also strongly decreases with increasing shear rate. The viscosities of emulsions having 80 to 95 percent internal phase are in the following ranges when measured between two parallel plates at 25° C.

| Shear rate ($s^{-1}$) | Viscosity (Pa · es) |
|---|---|
| 0.01 | 1000–5000 |
| 1 | 40–300 |
| 100 | 3–10 |

The support material employed to produce laminates or other end products can be of any type that would allow spreading of the formulation of the emulsion, containing the needed crosslinker and other needed additives onto the support material, to be dried and cured. Preferably, those support materials or combinations of support materials used are those typically used in any absorbent devices. Suitable support materials include, for example, nonwoven fabrics (used as top sheets), fluff pads, plastic films, such as, for example, back sheets, or any foam sheets, such as, for example, high internal phase emulsion foams, polyurethane foams, latex froth foams or the like. Other possible materials include fibers, glass, ceramic, metal, or indeed any other surface where it may be advantageous to have a superabsorbent material.

The polymers of the invention can be used to form a pure SAP film, for example, by casting the polymer onto a metal or ceramic plate, or onto a plastic film, such as a Mylar film. Then, after the film has dried, the film can be peeled from the support. Such films may advantageously be of thickness ranging from 0.01 mm up to 1 mm, or even more. A film prepared in this way can then be used in other structures. Thus, the SAP film may be placed onto one nonwoven fabric sheet, or between sheets which can be the same or a combination of different materials. Similarly, it should be understood that such SAP layers may be placed on foam sheets or plastic films or combinations of these materials, as may be desired for particular end use applications. Articles incorporating more than one SAP can be prepared from the polymers of the invention.

In addition to SAP films there are other forms the material may take. For example the SAP may be spread or printed or extruded or otherwise formed into various patterns. The pattern can be dots, lines, grids, or any geometric figure. Size, shapes and the density of the distribution of the pattern can be varied. The particular pattern and density of SAP material will influence the absorption rate, so that liquid distribution and total absorption capacity of the absorbent structure can be maximized. For example, lines of SAP will allow channels to form which may advantageously allow some moisture to be dispersed to other areas of the absorbent product. Similarly the spacing and size of dots can be printed onto the substrate in complex patterns to facilitate the even distribution of liquid, maximizing the total absorption capacity and minimizing the time required to absorb a given amount of liquid.

It should also be understood that the particular SAP can be different over different areas of the end product as well, giving the designer further ability to optimize the final product. Thus, it is conceivable to have a SAP which features rapid absorption rates on one area of the product and a different SAP which exhibits high absorption capacity on another area of the product. Accordingly, it should be realized that the new polymers and processes of the present invention allow the SAP to be precisely distributed on or within a support material, so that new products can be designed which optimize absorption capacity, the rate of absorption, the distribution of liquids, and product integrity after swelling. Thus the present invention not only has application in human absorbent devices (such as baby diapers, adult incontinence devices, and feminine hygiene applications), but also other SAP areas such as cable wrap, agricultural uses, medical uses, packaging, and in fact any other application in which absorption, retention or slow release of aqueous liquids is desired.

The high internal phase emulsions of the present invention can also be used in applications other than SAP's, such as, for example, as flocculants or clarifying agents, thickening agents, and dispersants.

Experimental Section

The water-in-oil emulsions were prepared in accordance with the generic recipe displayed in Table 1 or Table 5. Modifications of the individual emulsion compositions were made in accordance to the footnotes given in Table 1 and as further specified in the examples to follow. All parts and percentages are by weight unless otherwise indicated.

I) Preparation of the Aqueous Phase

The total amount of 20 percent by weight sodium hydroxide solution as required according to the recipe, was weighed into a glass beaker of appropriate size and the fraction of 65–70 percent by weight of the total weight of acrylic acid as specified in the recipe was added at a controlled rate under continuous mixing. The temperature of the solution was monitored and controlled by cooling with an ice bath and by adjusting the acid addition rate so as to not exceed 35° C. VERSENEX 80 chelating agent (Trademark of The Dow Chemical Company) was added to the partially neutralized acid.

Thereafter, the remaining amount of acrylic acid (30–35 percent) was added, while stirring, to obtain the desired neutralization degree (that is 68 percent). All the other additives including one or more crosslinkers, if desired, were added to the monomer mix at this point. A clear homogeneous solution was obtained that was used on the day it was prepared.

II) Preparation of the Oil Phase

The required amount of the hydrophobic organic solvent was weighed into a plastic beaker together with the desired amount of the emulsion surfactant (usually Hypermer B246). The two components were mixed while warming them up to about 60° C. to obtain a homogeneous solution.

III) Emulsification of the Phases

In order to get a desirable emulsion the aqueous phase preferably is added to the oil phase. However, optionally, the oil phase may be added to the aqueous phase. Continuous agitation of the mixture is required during addition in order to provide the shear forces required for the formation of the dispersed particles. Excessive shear, however, can break the emulsion. The conditions of emulsification and demulsification depend largely on the phase ratio. Therefore, careful adjustment of the intensity of shear is required for various formulations and can be readily determined by trial and error.

Procedure 1

Emulsification is carried out with the aid of a high speed emulsifier (Ultra Turrax type TP 18/10, equipped with the dispersing tool S 25N 18G from Jahnke & Kungel, IKA Werk, Germany). For speed control, the emulsifier was also equipped with a special controller (Thyristor controller Type TR 50 available from the same company).

The aqueous monomer mix is then fed into the oil phase (solution of surfactant(s) in the organic solvent) during about 30 seconds and stirred for an additional 10 minutes at the same speed. A homogeneous emulsion is obtained which is typically transferred into the reactor for polymerization.

Procedure 2

Emulsification is carried out with the aid of a magnetic stirrer. The organic phase in a beaker of suitable size is stirred intensely with an magnetic bar on a magnetic stirrer and the aqueous phase is added over a time period of about 30 seconds. Mixing is continued for an additional 10 minutes. For the polymerization, the emulsion obtained is transferred to a reactor.

Procedure 3

This emulsification is carried out in the reactor with the aid of an anchor stirrer. The organic phase is placed in the reactor (250 ml or one-liter size), agitated with the anchor stirrer and the aqueous phase is added over a time period of about 30 seconds and stirred for a another 10 minutes.

Procedure 4

Procedure 1 is repeated except that after the 30 second period of addition, the mixture is stirred for approximately 1 minute at speed setting number 4.

IV) Polymerization

In a 1-liter glass reactor, equipped with a anchor stirrer, heating gasket, a reflux condenser, a dip pipe for nitrogen purge and a thermocouple, the emulsion is adjusted to a temperature of 25° C. For de-oxygenation of the monomer, the emulsion is purged with nitrogen gas while continuously stirring for 1 hour at a speed of 200 rpm. Thereafter, the nitrogen flow is decreased and the pipette raised to just above the surface of the emulsion to maintain a nitrogen atmosphere over the reaction mixture. The reaction is then initiated by raising the water bath temperature to 35° C. During the exothermic polymerization reaction, the water bath temperature is raised in line with the actual reaction temperature until the reaction temperature peaks at about 70° C. This temperature is held for 1 hour to complete the conversion of monomer to polymer. The emulsion is agitated during polymerization at a speed between 60 and 200 rpm, depending on the phase ratio. During the hold time, the emulsion is only slightly agitated or agitation is halted. Thereafter, the emulsion is cooled to room temperature and discharged into a bottle.

V) Characterization of the Emulsion

A) Viscosity

The viscosity of the emulsion is determined using a Rheometrix RFS 8500 Rheometer equipped with two parallel plates having a diameter of 50 mm. An emulsion sample is placed between the two parallel plates having a separation distance of 1 mm and is adjusted to a temperature of 25° C. The viscosity is determined at shear rates in the range of $10^{-3}$ to $10^3$ $sec^{-1}$. The viscosity given in the Examples has been determined at a shear rate of $1 \cdot sec^{-1}$. In some Examples which had low viscosity emulsions, the viscosity was determined using a Brookfield viscometer. Specific conditions are given in the respective Examples.

B) Molecular Weight of the Polymer

The molecular weight of the polymers was determined using a size exclusion chromatography method. This procedure uses a single TSK GMPWXL column and the flow rate is set to 0.5 mL/min. Detection is by refractive index and quantitation using PL Caliber™ GPC/SEC software version 6.0 from Polymer Laboratories inc. Calibration is performed with polyethylene oxide standards obtained from Toso-Haas. A precision of +/−3.28 percent over a two day period at the 95 percent confidence level was found. It was determined that narrow molecular weight distribution polyethylene oxide standards obtained from Toso-Haas generated very similar calibration curves as polyacrylic acid standards obtained from American Polymers.

C) Residual Monomer

A sample of 1.786 grams of the emulsion is combined with 92.5 ml of a solution of 55 percent by weight of acetone in 45 percent by weight of water. During the addition of the emulsion, the mixture is intensely agitated by a high speed homogenizer (Ultra Turrax). The polymer is insoluble in the mixture of solvents and precipitates as a fine powder.

The mixture is put on the shaking machine overnight and the resulting extract is injected into a liquid chromatograph.

Separation is made on a cation exhange column and the efluent is monitored with an ultraviolet detector. Quantification is made by peak areas measurement using external standard calculations with a computing integrator.

D) Particle Size

The particle sizes of the SAP's of the present invention were determined by the scanning electron microscopy (SEM) technique followed by Image analysis.

TABLE 1

Recipe for 1 kg Water-in-Oil Emulsion having 90 Percent Aqueous Phase

| Ingredient | Weight(g) | Concentration in Formula. | Comments |
|---|---|---|---|
| Aqueous Phase*[1] 80 percent, based on total | | | |
| Acrylic acid (AA) | 263.44 | 29.27 | wt percent b.o. aqueous Phase |
| Sodium hydroxide (20 percent aq.) | 497.62 | | |
| Water | 132.03 | | |
| Crosslinker[2] | | | |
| Versenex 80 | 0.33 | 500 | ppm b.o. AA |
| Sodium persulfate | 4.48 | 1700 | ppm b.o. AA |
| Hydrogen peroxide[3] | | | ppm b.o. AA |
| 2,2'-Azobis(2-amidinopropane) dihydrochloride[4] | 2.11 | 800 | ppm b.o. AA |
| TOTAL | 900.00 | | |
| OIL PHASE | | | |
| Isopar L[5] | 264.60 | 9.26 | wt percent b.o. emulsion |
| Surfactant[6] Hypermer B246 | | 0.745 | wt percent b.o. aqueous phase |
| TOTAL | 100.00 | | |

*35 percent by weight solids, based on aqueous phase
[1]Varied from 73 to 95 percent;
[2]Optional;
[3]Varied from 0 to 1400 ppm;
[4]Commercially available from Wako Chemicals under the tradename V-50;
[5]Other types of hydrophilic organic solvents have also been used;;
[6]Varied between 0.4 to 2 percent.

EXAMPLE 1

Preparation of a 73 Percent Internal Phase Emulsion

An amount of 730 grams of aqueous phase was combined with 270 grams of oil phase. Both phases were prepared according to the composition given in Table 1. The phases were emulsified at the highest possible speed (setting 10=20,000 rpm) according to Procedure 1. The temperature reached at the peak (Tpeak) was 76° C. The emulsion obtained was of low viscosity and, therefore, free flowing. The viscosity of the emulsion was 108 mPa·s, measured with a Brookfield RVT viscometer at 20° C. with a #2 spindle. The molecular weight of the polymer was Mw=3,380,000 g/mole having a dispersity (D) of 2.65. The dispersed particles had a size between 0.6 and 7.5 microns with an average of 1.5 microns.

EXAMPLE 2

Preparation of a 80 Percent Internal Phase Emulsion

The same procedure was followed as for Example 1, except that 800 grams of aqueous phase and 200 grams of the organic phase were combined. The reaction reached a peak temperature (Tpeak) of 84° C. The emulsion obtained was of low viscosity and, therefore, free flowing. The viscosity of the emulsion was 8,440 mPa·s, measured with a Brookfield RVT viscometer at 20° C. with a #5 spindle. The molecular weight of the polymer was Mw=3,990,000 g/mole having a dispersity (D) of 2.15. The dispersed particles had a diameter between 0.5 and 7.1 microns with an average of 1.6 microns.

COMPARATIVE EXAMPLE Example A

Preparation of a 95 Percent Internal Phase Emulsion (Not an Embodiment of the Invention)

The same procedure was followed as for Example 1, but with the following exceptions: 1,900 grams of aqueous phase and 100 grams of the organic phase were combined; the phases were emulsified by adjusting the homogenizer speed to 6 instead of 10. The reaction peaked at about 100° C. Due to the high viscosity of the emulsion nitrogen purging of the monomer emulsion was not homogeneous and de-oxygenation, therefore, insufficient. The emulsion obtained had a consistency of a paste (viscosity=750 Pa·s). The molecular weight of the polymer was Mw=1,322,400 g/mole having a dispersity (D) of 3.74. The dispersed particles had a diameter between 0.5 and 7.0 microns with an average of 2.2 microns.

EXAMPLE 3

Preparation of a 95 Percent Internal Phase Emulsion

The same procedure was followed as for Comparative Example A, except that the phases were emulsified in a one-liter glass reactor by applying the Emulsification Procedure 3. The agitator speed was set to 250 rpm during emulsification and to 60 rpm during polymerization. The reaction peaked at about 100° C. The emulsion obtained had the consistency of a paste (viscosity=251 Pa·s). The molecular weight of the polymer was (Mw=2,730,000 g/mole, having a dispersity (D) of 3.83. The dispersed particles had a diameter between 0.3 and 24.5 microns with an average of 2.1 microns. Compared to Comparative Example A, the shear used during emulsification in Example 3 was more appropriate to keep the emulsion stable and of acceptable viscosity. This will be advantageous for, for example, the $N_2$ purging.

EXAMPLE 4–7

Preparation of a 80 Percent Internal Phase Emulsions

The same procedure was followed as for Example 2, except that different organic solvents were applied. For these Examples, the reactor was equipped with a reflux condenser in order to prevent solvent loss during nitrogen purging and polymerization. The properties of these emulsions are summarized in Table 2.

TABLE 2

| Ex. No. | Solvent | Viscosity (Pa · s) | Mw, g/mole | D | Particle Size (PS), microns | Avg. PS Distribution, microns | Tpeak |
|---|---|---|---|---|---|---|---|
| 4 | Cyclohexane | too gelly* | 4,070,000 | 1.93 | 0.4–7.6 | 1.4 | 70.8 |
| 5 | n-Heptane | 190 | 3,290,000 | 3.04 | 0.5–5.0 | 1.8 | 71 |
| 6 | Nonane fract. | 290 | 2,790,000 | 3.04 | 0.5–5.3 | 2.0 | 80.8 |
| 7 | Isopar L | n.m. | 3,990,000 | 2.15 | 0.5–7.1 | 1.6 | 83.7 |

*Too gelly means that the viscosity of the emulsion was too high (it partly collapsed) so that the viscosity could not be measured on the equipment employed.
n.m.—too viscous to be measurable under the measurement conditions EXAMPLE 8 and 9

The same procedure was applied as for Example 2, except that the concentration of the monomer in the aqueous phase was changed, heptane was used as the organic solvent and the reactor was equipped with a reflux condenser to prevent solvent less during nitrogen purging and polymerization. The properties of these emulsions are summarized in Table 3.

TABLE 3

| Example No. | Conc. of aqueous phase | Viscosity (mPa · s) | Mw (g/mole) | D | Tpeak |
|---|---|---|---|---|---|
| 8 | 30 percent | 355 | 2 981 000 | 3.71 | 71 |
| 9 | 37.5 percent | 477 | 3 344 000 | 5.76 | 81 |

VI) Inversion Techniques

As mentioned before, the inversion of the high internal phase emulsions of the present invention may be accomplished using several different techniques among which are the following:

1) Solvent Extraction

The polymer beads of the emulsion can be separated from the oil phase and dried by the solvent extraction method. The emulsion is mixed with a hydrophilic, organic solvent. The oil phase, the surfactant and most of the water of the aqueous gel beads dissolve in the solvent and the substantially water-free polymer is separated and further dried to obtain a powder. The post crosslinker can be mixed with the powder and the mixture can be spread into the desired shape either dry or as a slurry in a suitable organic solvent. The powder layer is then wetted and allowed to stand for a time sufficient to allow the formation of the desired gel matrix which then can be crosslinked and dried by heating. The advantages of this procedure are that the solvent is removed at the earliest point in time and that the surfactant is removed from the polymer.

2) Evaporation of the Organic Phase

This procedure can be applied for water-in-oil emulsions with an oil phase having a boiling point below 100° C. These solvents form azeotropes with water such that the major component of the vapor consists of the organic solvent. The solvent can, therefore, easily be removed leaving most of the water in the gel beads. This is important, since the water must be present for the formation of the gel matrix. Additional water may be required.

When following this procedure, the crosslinker is mixed with the emulsion, and the mixture is directly spread into the final shape. The solvent is azeotropically distilled off. The remaining layer is held for a time to allow the diffusion of the polymer molecules. Thereafter, the structure is heated to crosslink and dry the polymer.

3) Application of a High HLB Surfactant

The process of inverting water-in-oil emulsions using surfactants is well known. It is applied to prepare solutions of flocculants, such as polymers and co-polymers of acrylamide from water-in-oil emulsions (see, for example, U.S. Pat. No. 3,624,019). These emulsions are provided with a surfactant system which inverts the emulsions immediately after mixing them with an excess of water. Normally, solutions of less than 3 percent solids are prepared in this way. Inversion is enabled by the addition of an inversion surfactant having a high HLB value, that is, an HLB number of more than 10. In the present invention, the inversion with high HLB surfactants is achieved by adding less than 25 weight percent, preferably less than 15 weight percent, water or water-soluble organic solvents, based on the total emulsion.

4) Application of LCST Solvents

The inclusion of solvents that change in hydrophobicity as temperature changes, allow for temperature controlled inversion of the emulsions. Dipropylene glycol dimethyl ether becomes more hydrophobic with increasing temperature, causing the emulsification agent to partition into the oil phase. This causes the emulsion to break and the formation of a solid glassy gel. Similarity, 1,2-hexanediol becomes more hydrophobic with decreasing temperature, breaking the emulsion and forming a solid glassy gel. The amount and type of solvent can be adjusted and or modified to achieve temperature controlled processing of the emulsion into useful products.

5) Application of Metal Oxide Powders

Another preferred route to invert the emulsions of the present invention includes the application of metal oxides, such as titanium dioxide, fumed silica and other particulate oxides. Concentrations in the range of 0.5–5 percent by weight based on the weight of the emulsion can be employed. After the metal oxide is mixed with the emulsion, sufficient time is given to shape the desired structure before inversion begins.

VII) SAP Structure Evaluation Methods:

VII-A) Evaluation of Ground SAP Films

VII-A-1) Centrifuge Retention Capacity (CC):

200 mg of water-absorbent resin particles, obtained from ground SAP films, patterns or structures, are sieved to a size range of 30–50 mesh, are placed within a sealable tea bag (63.5×76.2 mm), immersed for 30 minutes into a 0.9 percent saline solution and then centrifuged for three minutes at 1600 rpm. The weight ratio of saline solution absorbed to water-absorbent resin particles is the centrifuge retention capacity (CC).

VII-A-2) Absorbency Under Load (AUL)

The test apparatus consists of a plastic cylinder, with a wire cloth (100 mesh) fastened across the bottom of a cylinder, a liquid reservoir, and a cell holder equipped with a porous plate. The liquid reservoir is filled with 0.9 weight percent aqueous NaCl. The apparatus is adjusted so that the height of the liquid meniscus in the reservoir and porous plate are equalized. A piece of filter paper (GF/A glass filter paper circles of 2.4 cm diameter) is placed on the porous plate to ensure good contact of the liquid with the polymer while minimizing evaporative losses.

160 mg of water-absorbent resin particles was ground and sieved to a size range of 30–50 mesh, and then was placed into the cylinder and evenly distributed and pressed down with a piston which carries a mass (typically 100, 200 or 317 grams for 2.0, 3.9 and 6.2 kPa loads, respectively). The grouping of cell and mass was placed onto the porous plate, which was covered with the filter paper. The mass loss of the reservoir or the mass gained of the sample was recorded to determine the swelling as a function of time and applied pressure.

VII-A-3) Extractables 1 g of water-absorbent resin particles and 185 mL of 0.9 percent saline solution are placed in an 250 mL jar which is capped and put on a shaker for 16 hours. A part of the extraction solution is filtered. With the aid of a Metrohm Titro-processor the pH of a defined volume of the filtrate is adjusted to pH 10 by 0.1 normal NaOH and finally titrated to pH 2.7 by 0.1 normal hydrochloric acid, to determine the amount of residual monomer which is in the filtrate.

VII-B) Evaluation of SAP Structures and Laminates
VII-B-1) Centrifuge Retention Capacity (CC)

This method is a modified version of the test method described under VII-A-1. The sample contained in a teabag is immersed for 60 min in 0.9 weight percent NaCl solution and then centrifuged for 3 min. The retention capacity is calculated as the difference between the teabag weight after centrifugation minus the blank teabag after centrifugation, divided by the sample weight before immersing in saline solution, and is expressed in grams saline solution retained per gram sample.

VII-B-2) Absorbency Under Load (AUL)

This test method is the same as the one for ground SAP, except for using a square container having 10 cm ×10 cm dimensions.

VII-B-3) Extractables

A sample of SAP is titrated with 0.1 N hydrochloric acid. The total amount of extractables in the sample is related to the volume of 0.1 N hydrochloric acid used to change the pH of the solution from 10 to 2.7.

VII-B-4) Absorption Rate

This method determines the absorption rate of composite samples made of SAP on a substrate support material, such as foam or nonwoven fabric, and is expressed in gram absorbed solution of 0.9 percent by weight NaCl per gram composite (support material/SAP) or SAP.

EXAMPLE 10

SAP by the Solvent Extraction Route

Acetone (200 g) was mixed with 35 g of the emulsion of Example 1 using the Ultra-Turrax high shear mixer at speed 6 for 2.5 minutes to substantially extract the water and emulsion surfactant from the aqueous gel beads. The polymer was allowed to settle and form flakes. The supernatant solution containing acetone, water, emulsion surfactant and oil was poured away and the flakes were redispersed in propan-2-ol (100 g) using the Ultra-Turrax at speed 9 for 3 minutes. The dispersed polymer in propan-2-ol was then centrifuged at 2800 rpm for 5 minutes using a Heraeus Varifuge GL centrifuge. The clear propan-2-ol was then poured away. Propan-2-ol (4 mL) was then added to the polymer/propan-2-ol mass to produce a slurry. A portion of 20 mg of glycerin (2000 ppm based on solids) was then added to this slurry and stirred for approximately 3 minutes to obtain an even distribution. Films were made on a film drawing machine using wire-coiled bars of 300–600 µm specification. The films were allowed to stand in a fume hood to allow most of the propan-2-ol to evaporate, resulting in "powder films."

The "powder films" were then put into a high humidity cabinet at 95 percent or more relative humidity for approximately 16 hours (overnight) to allow the polymer to hydrate and diffuse to form continuous films. After hydration, the films were put into the oven at 190° C. for 20 minutes to crosslink them. The dry film had a thickness of 0.149 mm and a CC of 28.8 g/g. The film had a very good stability when swollen.

COMPARATIVE EXAMPLES 11 and 12

SAP by Evaporation of the Oil Phase (not embodiments of the invention)

A portion of 100 grams of an emulsion, each prepared according to the description of Examples 4 and 5, respectively, was mixed with 70 mg of ethylene glycol diglycidyl ether (2000 ppm based on solids), and spread onto a Mylar film to achieve a thickness of 1 mm. The films were stored overnight in an atmosphere of 95 percent relative humidity and, thereafter, dried in the oven at 120° C. for 30 minutes.

There was no continuous film formed, but instead a loosely agglomerated fine powder.

EXAMPLE 13

SAP Formation on a Mylar Film by Emulsion Inversion)

A portion of 100 grams of an emulsion prepared according to the description of Example 5, was mixed with 70 mg of ethylene glycol diglycidyl ether (2000 ppm based on solids) and 0.8 percent by weight of an inversion surfactant, Softanol 70, commercially available from BP Chemicals, and well mixed with a spatula. Then, 7.5 percent of water was added and also well mixed. Thereafter, the formulation was spread onto a Mylar film, kept overnight in an atmosphere of 95 percent relative humidity and then, the gel film that was formed was dried in the oven at 120° C. for 30 minutes. The film had a CC of 26.4 g/g, an AUL at 0.3 psi of 18.4 g/g and an extractables level of 2.9 percent.

EXAMPLE 14

SAP Formation on a Nonwoven Fabric by Emulsion Inversion

A portion of 100 grams of an emulsion prepared according to the description of Example 5, was mixed with 70 mg of ethylene glycol diglycidyl ether (2000 ppm based on solids) and 1.2 percent by weight of Softanol 70 and well mixed with a spatula. Thereafter, the formulation was spread onto a Mylar film, and covered with a nonwoven fabric that was previously immersed in water before. This procedure provided 27.1 percent of water to the film on the Mylar foil. This structure was kept overnight in an atmosphere of 95 percent relative humidity. Then, the Mylar film could easily be peeled off and the gel film on the nonwoven fabric dried in the oven at 120° C. for 30 minutes. The film had a CC of 26.3 g/g, an AUL at 0.3 psi of 12.5 g/g and an extractables level of 2.3 percent.

EXAMPLE 15

Application of Fumed Silica; n-Heptane

A portion of 100 grams of an emulsion prepared according to the description of Example 5 was mixed with 70 mg of ethylene glycol diglycidyl ether (2000 ppm based on solids) and 1 g (2.8 percent by weight, based on solids) of Aerosil 972, fumed silica, obtained from Degussa, with the aid of a spatula. Thereafter, the formulation was spread onto a Mylar film, held for one hour under ambient conditions and finally dried in a forced air oven at 120° C. for 30 minutes. The film had a CC of 25.8 g/g, an AUL under 0,3 psi of 19.3 and 8.9 percent extractables.

EXAMPLE 16

SAP Pattern on Nonwoven Fabric; Retarded Absorption

A portion of 100 grams of emulsion prepared according to the description of Example 5, was mixed with 70 mg of ethylene glycol diglycidyl ether (2000 ppm based on solids) and 1 g (2.8 percent by weight, based on solids) of fumed silica which was dispersed in 7.5 grams of n-heptane. The mixture was spread in the form of distinct pattern onto a dry nonwoven fabric which is usually applied as a top sheet for diapers. A perforated metal plate of one mm thickness with dimensions of 20 mm length and 2 mm width and having regularly distributed openings, was used to print the pattern. The structure obtained was left at ambient conditions for one hour and finally dried and cured in the oven at 120° C. for 30 minutes. The superabsorbent polymer has a CC (after one hour soak time) of 21.2 g/g and an AUL of 15.3 g/g. The structure showed a retarded absorption and a reduced absorption rate as expressed in the AUL data as shown in Table 4.

TABLE 4

| Absorption Time (seconds) | AUL (g/g SAP) |
| --- | --- |
| 100 | 0 |
| 200 | 1 |
| 600 | 7.5 |
| 3600 | 15.3 |

After swelling, the SAP patterns were still fixed to the nonwoven fabric.

EXAMPLE 17

A portion of 100 grams of an emulsion prepared according to the descriptions of Example 2, was mixed with 5 percent by weight of dipropylene glycol dimethyl ether. The mixture was spread 0.127 mm (5 mils) thick on a Mylar film on a temperature gradient plate for three hours. A slow flow of dry nitrogen padded the sample. Sample temperatures reduced from ambient to 2° C.–10° C. or increased from ambient to 22° C. to 25° C. lead to inversions that produced tough transparent films.

TABLE 5

Recipe for 1 kg Water-in-Oil Emulsion having 80 Percent Aqueous Phase*

| Ingredient | Weight(g) | Concentration in Formula. | Comments |
| --- | --- | --- | --- |
| Aqueous Phase 80 percent, based on total | | | |
| Acrylic acid (AA) | 234.17 | 29.27 | wt percent b.o. aqueous Phase |
| Sodium hydroxide (20 percent aq.) | 442.33 | | |
| Water | 117.36 | | |

TABLE 5-continued

Recipe for 1 kg Water-in-Oil Emulsion having 80 Percent Aqueous Phase*

| Ingredient | Weight(g) | Concentration in Formula. | Comments |
| --- | --- | --- | --- |
| Crosslinker | | | |
| Versenex 80 | 0.29 | 500 | ppm b.o. AA |
| Sodium persulfate | 3.98 | 1700 | ppm b.o. AA |
| 2,2'-Azobis(2-amidinopropane) dihydrochloride[1] | 1.87 | 800 | ppm b.o. AA |
| TOTAL OIL PHASE | 800.00 | | |
| n-Heptane | 198.16 | | |
| Surfactant B246 | 3.84 | 0.48 | wt percent b.o. aqueous phase |
| TOTAL | 200.00 | | |

*solid content of 35 percent, based on aqueous phase
[1]Commercially available from Wako Chemicals under the tradename V-50.

EXAMPLE 18

Preparation of a 80 Percent Internal Phase Emulsion

An amount of 800 grams of aqueous phase was combined with 200 grams of oil phase. Both phases were prepared according to the composition given in Table 5. The phases were emulsified at speed setting 4, according to Procedure 4. The temperature reached at the peak (Tpeak) was 83° C.

EXAMPLES 19–21

Application of Fumed Silica; n-Heptane Films

Three portions of 100 grams of an emulsion prepared according to the description of Example 18, were each mixed with 70 mg of ethylene glycol diglycidyl ether (1500 ppm based on solids) and 824 mg (2.8 percent by weight, based on solids) of Aerosil 972, fumed silica which was dispersed in 7.5 grams of n-heptane, obtained from Degussa, with the aid of a spatula. Thereafter, one of the portions of the formulation was spread directly onto a Mylar film (Example 19). The second portion was spread onto a nonwoven fabric (Example 20). The third portion was spread onto a foam sheet (Example 21. The films were made with a film drawing machine using wire-coiled bars of 650 µm specification. The films obtained were left at ambient conditions overnight and finally dried and cured in the oven at 120° C. for 30 minutes. The film properties are given in Table 6 below.

EXAMPLE 22

Application of Fumed Silica; n-Heptane-Film (No Gap)

A portion of 100 grams of an emulsion prepared according to the description of Example 18, was mixed with 70 mg of ethylene glycol diglycidyl ether (1500 ppm based on solids) and 824 mg (2.8 percent by weight, based on solids) of Aerosil 972 fumed silica which was dispersed in 7.5 grams of n-heptane, obtained from Degussa, with the aid of a spatula. Thereafter, the formulation was spread onto a nonwoven fabric. The film was made with a film drawing machine using wire-coiled bars having no gap. The film obtained was left at ambient conditions overnight and finally dried and cured in the oven at 120° C. for 30 minutes. The film properties are given in Table 6 below.

EXAMPLES 23 and 24

Application of Fumed Silica; n-Heptane Circular Pattern

Two portions of 100 grams of an emulsion prepared according to the description of Example 18, were each mixed with 70 mg of ethylene glycol diglycidyl ether (1500 ppm based on solids) and 824 mg (2.8 percent by weight, based on solids) of Aerosil 972, fumed silica which was dispersed in 7.5 grams of n-heptane, obtained from Degussa, with the aid of a spatula. Thereafter, one portion of the formulations was spread in the form of distinct patterns onto a dry nonwoven fabric which is usually applied as a top sheet for diapers (Example 23). The other portion was spread onto a foam sheet (Example 24). A perforated metal plate of one mm thickness having 175 regularly distributed openings per 10×10 cm, was used to print the pattern. The structures obtained were left at ambient conditions overnight and finally dried and cured in the oven at 120° C. for 30 minutes. The properties are given in Table 6 below.

EXAMPLES 25 and 26

Application of Fumed Silica; n-Heptane Stripe Pattern

Two portions of 100 grams of an emulsion prepared according to the description of Example 18, were each mixed with 70 mg of ethylene glycol diglycidyl ether (1500 ppm based on solids) and 824 mg (2.8 percent by weight, based on solids) of Aerosil 972, fumed silica which was dispersed in 7.5 grams of n-heptane, obtained from Degussa, with the aid of a spatula. Thereafter, one of the portions was spread uniformly onto a nonwoven fabric (Example 25). The other portion was spread onto a foam sheet (Example 26). With a spatula having square indentations on its blade a stripe pattern was carved in one direction only into the film. The structures obtained were left at ambient conditions overnight and finally dried and cured in the oven at 120° C. for 30 minutes. The properties are given in Table 6 below.

EXAMPLE 27

Application of Fumed Silica; n-Heptane Grid Pattern

A portion of 100 grams of an emulsion prepared according to the description of Example 18, was mixed with 70 mg of ethylene glycol diglycidyl ether (1500 ppm based on solids) and 824 mg (2.8 percent by weight, based on solids) of Aerosil 972, fumed silica which was dispersed in 7.5 grams of n-heptane, obtained from Degussa, with the aid of a spatula. Thereafter, the formulation was spread uniformly onto a nonwoven fabric. With a spatula having square indentations on its blade a stripe pattern was carved into the film in perpendicular directions so as to provide a grid pattern to the film. The structure obtained was left at ambient conditions overnight and finally dried and cured in the oven at 120° C. for 30 minutes. The properties are given in Table 6 below.

TABLE 6

| Example No. | CC, 60 min [g/g] Composite | CC, 60 min [g/g] SAP | AUL at 0.1 psi [g/g] Composite | AUL at 0.1 psi [g/g] SAP | Extractables, percent |
|---|---|---|---|---|---|
| 19 (Film) | — | 32.7 | — | — | — |
| 20 (Film on Nonwoven) | 16.2 | 17.7 | 17.7 | 18.5 | 4.9 |
| 21 (Film on Foam) | — | — | 6.0 | 3.7 | — |
| 22 (Film on Nonwoven - no gap) | 20.2 | 24.1 | 14.5 | 15.5 | 12.4 |
| 23 (Circular Pattern on Nonwoven) | 13.2 | 14.9 | 16.6 | 17.6 | 5.7 |
| 24 (Circular Pattern on Foam) | 7.1 | 14.1 | 13.4 | 14.1 | 7.0 |
| 25 (Stripe Pattern on Nonwoven) | 21.4 | 23.9 | 23.3 | 24.5 | 5.6 |
| 26 (Stripe Pattern on Foam) | 9.7 | 23.2 | 14.7 | 18.5 | 5.5 |
| 27 (Grid Pattern on Nonwoven) | 21.3 | 22.9 | 18.1 | 18.9 | 8.3 |

What is claimed is:

1. A process for preparing superabsorbent structures comprising:
    (a) preparing a high internal phase water-in oil emulsion comprising, in its aqueous dispersed phase, at least one hydrophilic monomer in aqueous solution and an initiator,
    (b) polymerizing the monomer in the aqueous dispersed phase to form a precursor polymer,
    (c) mixing the water-in-oil emulsion containing the precursor polymer with a post crosslinker and, optionally a plasticizing agent,
    (d) applying the emulsion resulting from step (c) onto a support material,
    (e) allowing or inducing coalescence of the aqueous phase under conditions sufficient to allow the emulsion to form a homogeneous polymer gel structure, and
    (f) drying and post crosslinking the formed gel material at a temperature sufficient to dry and cure the material, and
    (g) optionally, post-treating the material obtained in step (f) by post-heat treating the material, by surface modifying the material, by surface post-crosslinking the material, or by any combination of these post-treatments.

2. A process for preparing superabsorbent structures comprising:
    (a) preparing a high internal phase water-in oil emulsion containing, in its aqueous dispersed phase, a least one hydrophilic monomer in aqueous solution and a suitable initiator,
    (b) polymerizing the aqueous dispersed phase to form a precursor polymer,
    (c) mixing the water-in-oil emulsion containing the precursor polymer with a post-crosslinker, an inversion agent, and, optionally a plasticizing agent,
    (d) spreading or casting the emulsion resulting from step (c) on a support material into a film, shape or pattern,
    (e) allowing the spread or cast emulsion to invert from a water-in-oil emulsion into a oil-in-water emulsion for a time sufficient to allow the emulsion to invert and for the polymer material to form a homogeneous polymer gel structure, and (f) drying and post crosslinking the formed gel material at a temperature sufficient to dry and cure the material, and (g) optionally, post-treating the material obtained in step (f) by post-heat treating the material, by surface modifying the material, by surface post-crosslinking the material, or by any combination of these post-treatments.

3. A process according to claims 1 or 2 wherein the inversion of the emulsion can be accomplished by 1) solvent extraction, 2) evaporation of the organic phase, 3) application of surfactant(s) having a high hydrophilic lipophilic balance (HLB), 4) application of low critical solution temperature solvents, or 5) application of metal oxide powders.

4. A process according to claim 3 wherein the inversion of the emulsion is accomplished by solvent extraction.

5. A process according to claim 3 wherein the inversion of the emulsion is accomplished by evaporation of the organic phase.

6. A process according to claim 3 wherein the inversion of the emulsion is accomplished by the application of at least one surfactant having a high hydrophilic lipophilic balance (HLB).

7. A process according to claim 3 wherein the inversion of the emulsion is accomplished by the application of at least one low critical solution temperature (solvent.

8. A process according to claim 3 wherein the inversion of the emulsion is accomplished by the application of at least one metal oxide powder.

9. A process for preparing superabsorbent structures comprising:

(a) preparing a high internal phase water-in oil emulsion comprising in its aqueous dispersed phase, a partially neutralized-polyacrylic acid monomer in aqueous solution and a suitable initiator, (b) polymerizing the aqueous dispersed phase to form a precursor polymer having a particle size of from about 0.1 to 100 microns, (c) mixing the water-in-oil emulsion containing the precursor polymer with a post-crosslinker, an inversion agent, and, optionally a plasticizing agent, (d) spreading or casting the emulsion resulting from step (c) on a support material into a film, shape or pattern, (e) allowing the spread or cast emulsion to invert from a water-in-oil emulsion into a oil-in-water emulsion for a time sufficient to allow the emulsion to invert and for the polymer material to form a homogeneous polymer gel structure, and (f) drying and post crosslinking the formed gel material at a temperature sufficient to dry and cure the material, and (g) optionally, post-treating the material obtained in step (f) by post-heat treating the material, by surface modifying the material, by surface post-crosslinking the material, or by any combination of these post-treatments.

10. The process of claim 9 wherein the particle size is from 1 to 30 microns.

* * * * *